United States Patent [19]

Mizoguchi et al.

[11] Patent Number: 6,096,187
[45] Date of Patent: Aug. 1, 2000

[54] LIMIT CURRENT TYPE OXYGEN CONCENTRATION DETECTION HAVING OXYGEN SUPPLY/EXHAUST FUNCTION

[75] Inventors: Tomomichi Mizoguchi, Nagoya; Masayuki Takami; Syuichi Nakano, both of Kariya, all of Japan

[73] Assignee: Denso Corporation, Japan

[21] Appl. No.: 09/064,154

[22] Filed: Apr. 22, 1998

[30] Foreign Application Priority Data

Jun. 19, 1997 [JP] Japan ..................................... 9-162983
Feb. 24, 1998 [JP] Japan ................................... 10-042234

[51] Int. Cl.[7] .................................................... G01N 27/41
[52] U.S. Cl. ....................... 205/784.5; 204/408; 204/426; 204/427; 204/428
[58] Field of Search ..................................... 204/427, 426, 204/425, 408, 428; 205/783.5, 784, 784.5

[56] References Cited

U.S. PATENT DOCUMENTS

| 4,224,113 | 9/1980 | Kimura . | |
| 4,499,880 | 2/1985 | Miki et al. .............................. | 123/489 |
| 4,722,779 | 2/1988 | Yamada et al. ......................... | 204/425 |
| 4,765,880 | 8/1988 | Hayakawa et al. ..................... | 204/425 |
| 4,784,743 | 11/1988 | Iino et al. . | |
| 4,836,906 | 6/1989 | Yamada et al. ......................... | 204/425 |
| 4,882,033 | 11/1989 | Shibata et al. . | |
| 4,900,425 | 2/1990 | Sasayama et al. ...................... | 204/426 |
| 5,413,683 | 5/1995 | Murase et al. .......................... | 204/425 |

*Primary Examiner*—Robert J. Warden, Sr.
*Assistant Examiner*—Kai K. Olsen
*Attorney, Agent, or Firm*—Nixon & Vanderhye PC

[57] ABSTRACT

A detecting unit of an oxygen sensor as an A/F sensor has a solid electrolyte layer and a diffusion resistance layer and generates a current value according to the concentration of oxygen in an exhaust gas by applying a voltage across electrodes on an exhaust gas side and an atmosphere side of the solid electrolyte layer. An oxygen supply/exhaust unit has a solid electrolyte layer and a pair of electrodes formed on both faces of the solid electrolyte layer, and supplies oxygen near to the electrode on the atmosphere side of the detecting unit or exhausts oxygen near the electrode. A control unit controls, in response to a limit current value detected by a current detection unit, the amount of supply or exhaust of oxygen of the oxygen supply/exhaust unit on the basis of the detected current value. A control target value of a current flowing in the solid electrolyte layer is variably set so that amount of oxygen moving in the solid electrolyte layers are equal, thereby controlling the amount of supply or exhaust of oxygen of the oxygen supply/exhaust unit.

17 Claims, 8 Drawing Sheets

LIMIT CURRENT TYPE OXYGEN CONCENTRATION DETECTION HAVING OXYGEN SUPPLY/EXHAUST FUNCTION

CROSS REFERENCE TO RELATED APPLICATION

This application relates to and incorporates herein by reference Japanese Patent Applications No. 9-162983 filed on Jun. 19, 1997 and No. 10-42234 filed on Feb. 24, 1998.

BACKGROUND OF THE INVENTION

1. Field of the Invention

The present invention relates to oxygen concentration detection using an oxygen concentration sensor of a limit current type. The present invention may be used to detect an air-fuel ratio of air-fuel mixture from an oxygen concentration in exhaust gas of an engine.

2. Description of Related Art

A conventional air-fuel ratio detecting apparatus for instance, U.S. Pat. No. 4,224,113 (JP-A 55-62349) shown in FIG. 12 uses an oxygen concentration sensor as an air-fuel ratio sensor. In FIG. 12, an air-fuel ratio sensor 80 to be arranged in an exhaust pipe of a gasoline engine comprises: a diffusion resistance layer 81 exposed to an exhaust gas; a solid electrolyte layer 82 made of a known oxygen ion conductive oxide; electrodes 83a, 83b fixed to both faces of the solid electrolyte layer 82; a partition 85 for forming an atmosphere chamber 84; and a heater 86 embedded in the partition 85. In this sensor, the electrode 83a corresponds to an exhaust-side electrode and the electrode 83b corresponds to an atmosphere-side electrode.

FIGS. 13A and 13B show the fundamental principle of air-fuel detection by the air-fuel ratio sensor 80. Basically, a voltage Vp is applied across the electrodes 83a and 83b from a power source 87 and the value of a current flowing in this instance is detected, thereby detecting the air-fuel ratio. That is, when the air-fuel ratio is on the lean side (less fuel in air-fuel mixture supplied to an engine and more oxygen in the exhaust gas from the engine), as shown in FIG. 13A, the air-fuel ratio sensor 80 takes oxygen from the exhaust. In this instance, oxygen ions ($O^{2-}$) flow from the electrode 83a toward the electrode 83b. When the air-fuel ratio is on the rich side (more fuel in air-fuel mixture supplied to the engine and less oxygen in the exhaust gas from the engine), as shown in FIG. 13B, the air-fuel ratio sensor 80 takes unburned gas components such as CO from the exhaust. In this instance, oxygen ions ($O^{2-}$) flow from the electrode 83b to the electrode 83a. That is, the direction of oxygen ions flowing in the solid electrolyte layer 82 when the air-fuel ratio is on the rich side is opposite to that when the air-fuel ratio is on the lean sides. A limit current value Ip is positive at the time of the lean side and is negative at the time of the rich side.

FIG. 14 shows a V-I (voltage-current) characteristic of the air-fuel ratio sensor 80 having the above construction. FIG. 14A shows a V-I characteristic under a predetermined condition (lean). As shown in the diagram, in a zone where an applied voltage is low, a resistance characteristic of the solid electrolyte layer 82 is detected and the V-I characteristic shows a proportional relation. In a zone where the applied voltage is high, since movement of oxygen is regulated by the diffusion resistance layer 81, the current value is constant. The constant current value corresponds the limit current value. Generally, the zone showing the resistance characteristic is called a resistance dominating zone and the zone indicating the limit current value is called a limit current zone.

FIGS. 14B and 14C are characteristic diagrams showing change in the limit current value Ip corresponding to the change in the air-fuel ratio (A/F). According to FIG. 14B, as the air-fuel ratio changes, the limit current value Ip changes. It is understood that the more the air-fuel ratio shifts to the lean side, the larger the Ip value becomes. As shown by a characteristic line L1 of FIG. 14C, it is understood that since the relation between the air-fuel ratio and the limit current value Ip is a one-to-one corresponding relation, the air-fuel ratio can be detected from the limit current value Ip.

In the conventional air-fuel ratio detecting apparatus, however, when the air-fuel ratio is on the rich side, the following problem occurs. Although it is necessary to take oxygen from the atmosphere chamber 84 as shown in FIG. 13B when the air-fuel ratio is on the rich side, if the degree of richness is high, a large amount of oxygen is necessary. In such a case, the supply of oxygen from the atmosphere to the atmosphere chamber 84 is insufficient so that oxygen becomes deficient in the atmosphere chamber 84. When oxygen is deficient in the atmosphere chamber 84, oxygen does not flow any further, so that the limit current value Ip cannot be accurately detected. Consequently, as shown by a characteristic line L2 in FIG. 14C, the detection accuracy of the air-fuel ratio deteriorates when the air-fuel ratio is on the rich side. This may be caused because a passage to take atmosphere into the atmosphere chamber 84 is generally long and the atmosphere chamber 84 cannot be enlarged more than needed in order to secure a temperature increasing characteristic of the element by the heater.

When the air-fuel ratio is on the lean side, the following problems occur by similar reasons. That is, when the air-fuel ratio is on the lean side, as shown in FIG. 13A, oxygen is sent from the exhaust gas to the atmosphere chamber 84 on the contrary to the case where the air-fuel ratio is on the rich side. Consequently, when the degree of leanness is high, a large amount of oxygen flows into the atmosphere chamber 84. In such a case, the exhaust of oxygen from the atmosphere chamber 84 to the outside becomes insufficient, so that oxygen becomes excessive in the atmosphere chamber 84. When oxygen is excessive in the atmosphere chamber 84, the amount of oxygen passing through the solid electrolyte to the atmosphere chamber 84 is regulated, so that the limit current value Ip cannot be accurately detected. Consequently, as shown by a characteristic line L3 in FIG. 14C, the detection accuracy of the air-fuel ratio deteriorates when the air-fuel ratio is on the lean side.

On the other hand, according to U.S. Pat. No. 4,882,033 (JP-B2 4-73101), in order to cope with the problems due to oxygen deficiency, power supply unit for supplying oxygen into an atmosphere chamber (reference gas atmosphere) is provided. However, when the amount of oxygen flowing in the solid electrolyte layer changes due to change in the air-fuel ratio or the element temperature, the amount of oxygen in the atmosphere chamber cannot be maintained to a constant amount. Accordingly, the limit current value cannot be accurately detected and the air-fuel ratio detection accuracy deteriorates.

In U.S. Pat. No. 4,784,743 (JP-A 61-134656), an air-tight space communicating with an atmosphere chamber (gap) is provided so as to absorb fluctuation in the concentration of oxygen in the atmosphere chamber. Since the size of the atmosphere chamber is limited, the supply of oxygen from the air-tight space to the atmosphere chamber is insufficient. When the air-fuel ratio or the element temperature largely changes, the air-fuel ratio detection accuracy deteriorates. Although a partial voltage value of a heater voltage having a positive temperature characteristic is applied to oxygen supply unit so as to adjust an oxygen supply amount to the atmosphere chamber in accordance with a temperature change, the value to be applied depends on both of temperature characteristics of a heater resistor and an element resistor. Consequently, the oxygen amount depending only on the temperature characteristic of the element resistor cannot be controlled to be constant.

Consequently, in the conventional apparatuses shown in U.S. Pat. No. 4,882,033 and U.S. Pat. No. 4,784,743, the concentration of oxygen in the atmosphere chamber cannot be properly kept and the air-fuel ratio detection accuracy deteriorates when the air-fuel ratio or the element temperature changes.

SUMMARY OF THE INVENTION

It is an object to provide an oxygen concentration detecting apparatus and method which can accurately detect an oxygen concentration.

It is a further object of the present invention to provide an air-fuel ratio detecting apparatus and method which is suited to detect an air-fuel ratio of mixture from oxygen concentration in engine exhaust gas over a wide range of air-fuel ratio zone.

According to the invention, in order to achieve the object, a limit current type oxygen concentration sensor is used as an air-fuel ratio sensor. The sensor comprises an air-fuel ratio detecting unit which has a first solid electrolyte layer and a diffusion resistance layer which is in contact with the first solid electrolyte layer, a pair of electrodes formed on the first solid electrolyte. The sensor further comprises an oxygen supply/exhaust unit which has a second solid electrolyte layer and a pair of electrodes formed on both faces of the second solid electrolyte layer and supplies oxygen near to the electrode on the reference gas side of the air-fuel ratio detection unit or exhausts oxygen near the electrode to the outside. A current detection unit detects a value of a limit current flowing in the first solid electrolyte layer. A control unit receives the detected limit current value and controls the amount of supply or exhaust of oxygen of the oxygen supply/exhaust unit on the basis of the limit current value.

In short, in the limit current type air-fuel ratio sensor, when the air-fuel ratio changes from the stoichiometric ratio to the lean or rich side, oxygen ions flow in a predetermined direction in the first solid electrolyte layer and the flow of the oxygen ions is detected as a limit current. Specifically, when the air-fuel ratio of the gas to be measured is on the lean side, oxygen ions flow from the measured gas side to the reference gas side in the first solid electrolyte layer. On the contrary, when the air-fuel ratio of the measured gas is on the rich side, oxygen ions flow from the reference gas side to the measured gas side in the first solid electrolyte layer.

Since the oxygen supply amount in the oxygen supply/exhaust unit is controlled on the basis of the detected limit current value, for example, when the air-fuel ratio is on the rich side, the oxygen amount according to the degree of richness is supplied near to the electrode on the reference gas side. Consequently, fluctuation of the concentration of oxygen near the electrode on the reference gas side is suppressed and oxygen can be properly supplied near to the electrode on the reference gas side. That is, deterioration in the detection accuracy of the air-fuel ratio due to the oxygen deficiency can be solved.

Since the oxygen exhaust amount of the oxygen supply/exhaust unit can be controlled on the basis of the detected limit current value, for example, when the air-fuel ratio is on the lean side, the oxygen amount according to the degree of leanness can be exhausted from near the electrode on the reference gas. Thus, the fluctuation in the concentration of oxygen near the electrode on the reference gas side can be suppressed and the state of the excessive oxygen near the electrode on the reference gas side can be avoided. That is, deterioration in the air-fuel ratio detection accuracy due to the excessive oxygen can be solved.

Consequently, the air-fuel ratio can be accurately detected in any air-fuel ratio zone. Further, the atmosphere chamber for introducing the reference gas need not be enlarged more than needed and the temperature increasing characteristic of the element (solid electrolyte layer) does not deteriorate.

BRIEF DESCRIPTION OF THE DRAWINGS

Other objects, features and advantages of the present invention will become more apparent from the following detailed description when read with reference to the accompanying drawings. In the drawings.

DETAILED DESCRIPTION OF THE PREFERRED EMBODIMENT

Figure 1:
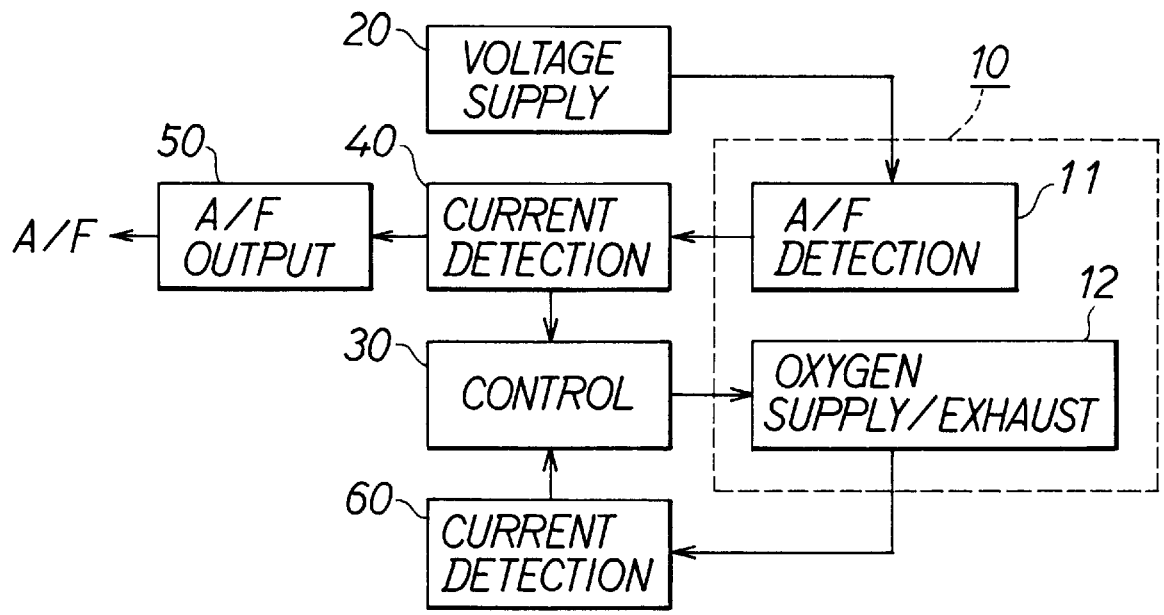
FIG. 1 is a block diagram showing an air-fuel ratio detecting apparatus according to a first embodiment of the present invention.

The present invention will be described in more detail with reference to air-fuel ratio detection for an engine. An air-fuel ratio detecting apparatus in the following embodiments 5 is to detect the air-fuel ratio of an air-fuel mixture gas supplied to a gasoline engine mounted on a vehicle and has a limit-current type oxygen concentration sensor as an air-fuel ratio sensor (an A/F sensor) for outputting a limit current corresponding to the air-fuel ratio at that time on the basis of oxygen concentration in the gas exhausted from the engine. Especially in the embodiments, in order to prevent an oxygen deficient state or an oxygen surplus state in a reference gas chamber (atmosphere chamber), oxygen is supplied to or exhausted from the reference gas chamber so that oxygen in the reference gas chamber is regulated to a necessary amount. Same or like reference numerals are used to designate the same or like parts throughout various embodiments shown in the drawings.

(First Embodiment)

In FIG. 1 showing an air-fuel ratio detecting apparatus, an A/F sensor 10 has an A/F detecting unit 11 which operates with application of a voltage by a voltage supply unit 20 and an oxygen supply/exhaust unit 12 which operates in accordance with a controlled variable from a control unit 30. A detection value obtained by the A/F detecting unit 11, that is, a limit current value according to the A/F ratio is detected by a current detecting unit 40. The current value detected by the current detecting unit 40 is outputted as an A/F value to a microcomputer for engine control (ECU) and the like via an A/F output unit 50.

A current detecting unit 60 detects the value of a current flowing in the oxygen supply/exhaust unit 12. The control unit 30 determines a controlled variable to the oxygen supply/exhaust unit 12 on the basis of the limit current detection value of the current detection unit 40 and the current detection value of the current detecting unit 60 and controls a amount of supply or exhaust of oxygen in the oxygen supply/exhaust unit 12 by the controlled variable. In the embodiment, the value of the current flowing in the oxygen supply/exhaust unit 12 corresponds to the controlled variable by the control unit 30.

Figure 2:
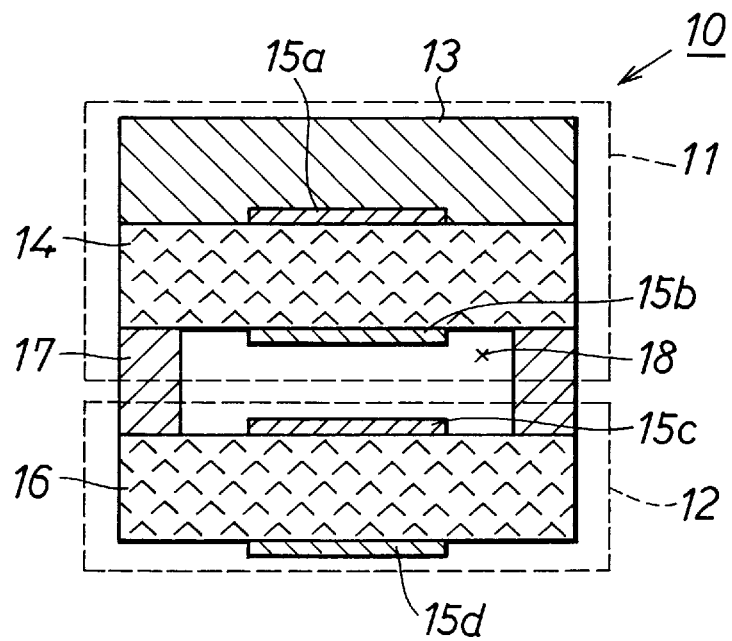
FIG. 2 is a cross sectional view showing an A/F sensor used in the first embodiment.

As shown in FIG. 2, the A/F sensor 10 itself is arranged in an exhaust as a gas to be measured. The A/F detecting unit 11 has: a diffusion resistance layer 13 made of a heat resisting inorganic material such as alumina, magnesia, silica, spinel, or mullite; a solid electrolyte layer (first solid electrolyte layer) 14 made of an oxygen ion conducting oxide sintered body which is solid-solved in a material such as $ZrO_2$, $HfO_2$, $ThO_2$, and $Bi_2O_3$ with a material such as CaO, MgO, $Y_2O_3$, and $Yb_2O_3$ used as a stabilizer; and a pair of upper and lower electrodes 15a and 15b fixed to the solid electrolyte layer 14.

The oxygen supply/exhaust unit 12 has: a solid electrolyte layer (second solid electrolyte layer) 16 made of the same material as that of the solid electrolyte layer 14; and a pair of upper and lower electrodes 15c and 15d fixed to the solid electrolyte layer 16.

An insulating ceramic layer 17 for partitioning an atmosphere chamber 18 is arranged between the solid electrolyte layers 14 and 16 of the A/F detecting unit 11 and the oxygen supply/exhaust unit 12. The insulating ceramic layer 17 is made of a heat resisting inorganic material such as alumina, magnesia, silica, spinel or mullite. Although the material is the same as that of the diffusion resistance layer 13, since the density of the material is higher than that of the diffusion resistance layer 13, oxygen does not pass through.

In the A/F sensor 10, the electrodes 15b and 15c are arranged in the atmosphere chamber 18 and correspond to the electrodes on the atmosphere side (electrodes on the reference gas side). The electrodes 15a and 15d correspond to the electrodes on the exhaust gas side (electrodes on the side of gas to be measured). The electrodes 15a to 15d are made of a noble metal with a high catalytic activity such as platinum and are formed as porous chemical plating on both faces of each of the solid electrolyte layers 14 and 16. The thickness of each of the electrodes 15a to 15d is about 0.5 to 2.0 μm.

Figure 3A:
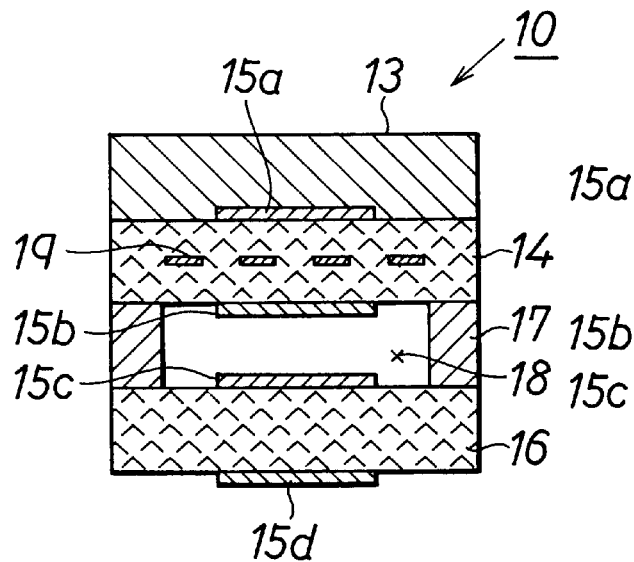
FIGS. 3A to 3D are cross sectional views of the A/F sensor having a heater.

The A/F sensor 10 needs heating unit for activating the sensor 10. According to the embodiment, as shown in FIG. 3A, a heater 19 is embedded in the solid electrolyte layer 14 of the A/F detection unit 11 and a voltage is supplied from a power source (not shown) to the heater 19. An electric power control and a feedback control for the heater 19 are performed according to resistance in an element (element temperature) in a known manner.

Figure 3B:
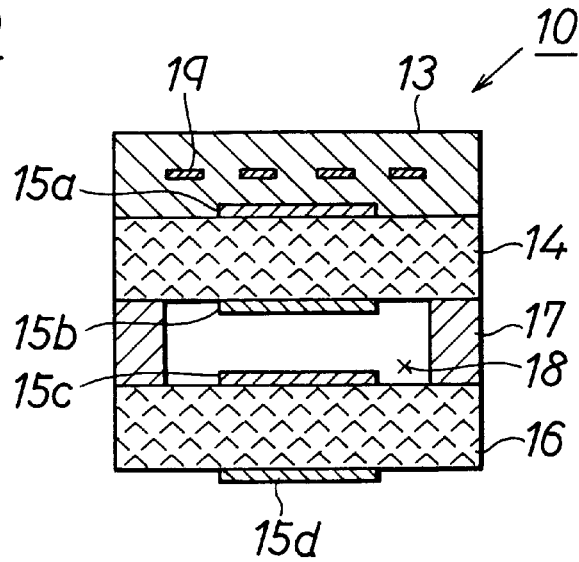
Figure 3C:
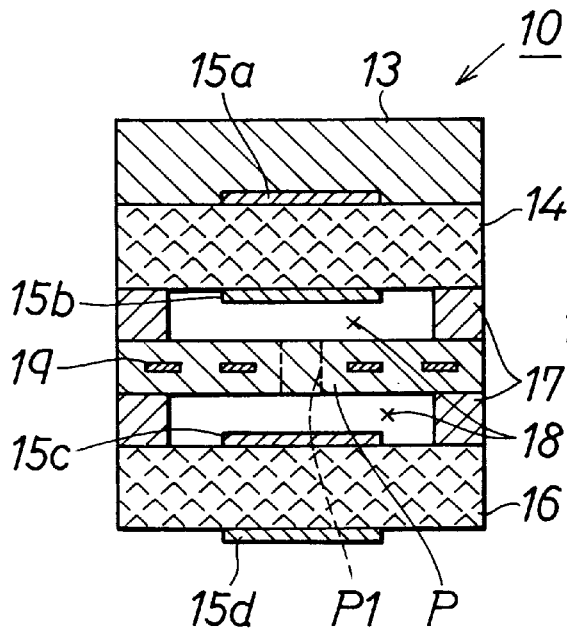
Figure 3D:
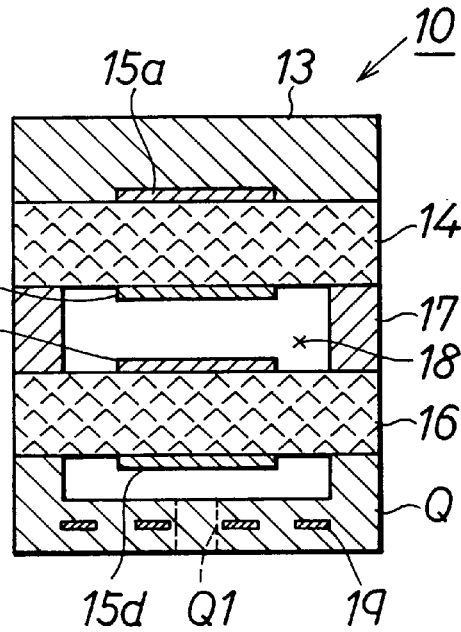

Alternative to FIG. 3A, the heater 19 can be also arranged as shown in FIGS. 3B, 3C, or 3D. In FIG. 3B, the heater 19 is embedded in the diffusion resistance layer 13. In FIG. 3C, the heater 19 is embedded in an insulating plate P between the two solid electrolyte layers 14 and 16. A through hole P1 is formed in the insulating plate P and the upper and lower atmosphere chambers 18 are communicated with each other via the through hole P1. In FIG. 3D, the heater 19 is arranged in a partition wall Q on the outside of the solid electrolyte layer 16. A through hole Q1 is formed in the partition wall Q and the under face of the solid electrolyte layer 16 is exposed to the exhaust gas via the through hole Q1. In order to assure the temperature increasing characteristic of the heater 19 and to realize quick activation of the A/F sensor 10, it is desirable to arrange the heater 19 near the solid electrolyte layer 14 of the A/F detection unit 11.

Figure 4:
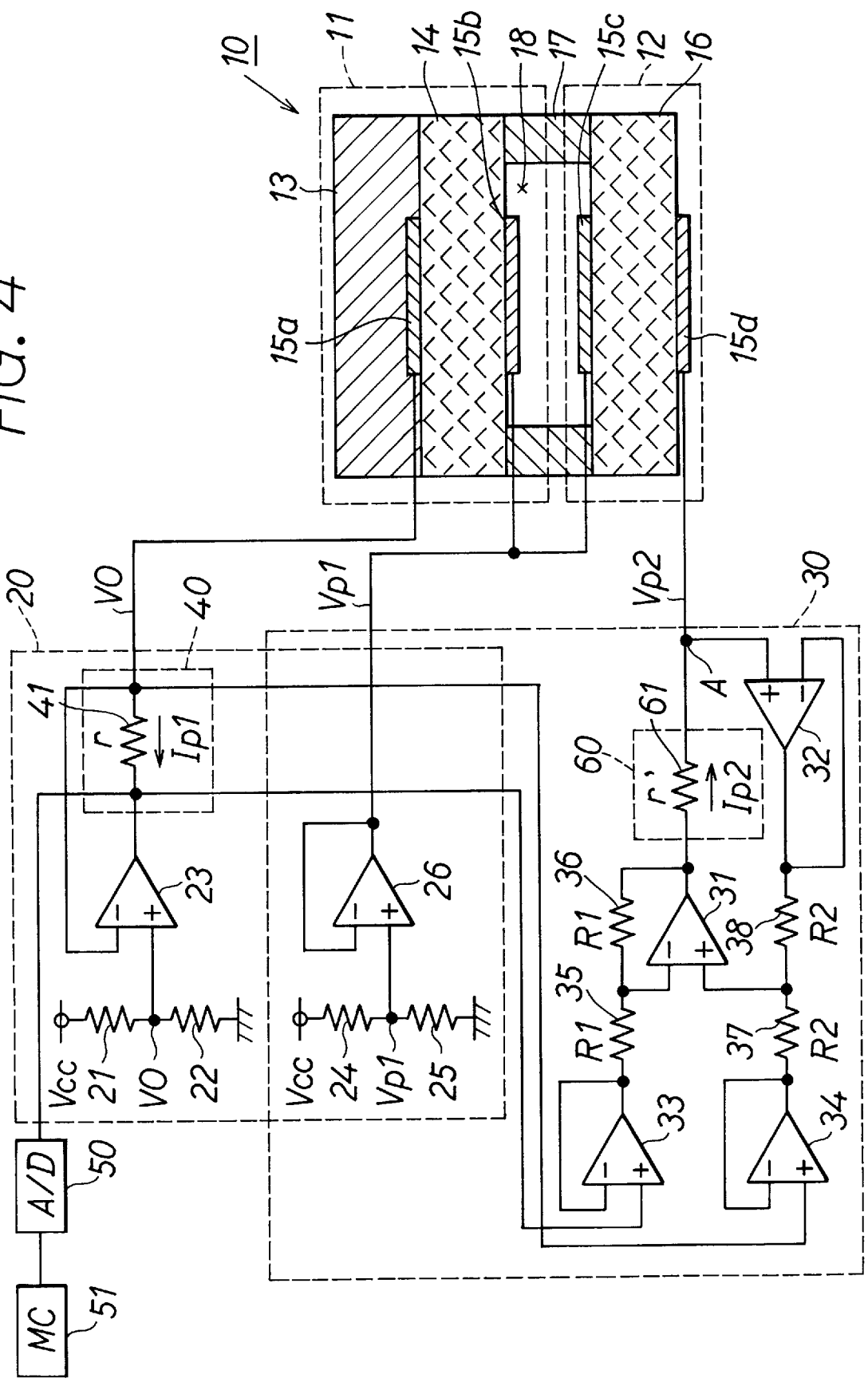
FIG. 4 is a circuit diagram showing an air-fuel ratio detecting apparatus.

FIG. 4 is a circuit diagram of the air-fuel ratio detecting apparatus according to the embodiment. The voltage supply unit 20 applies a predetermined voltage to the electrodes 15a and 15b when the air-fuel ratio is to be detected by the A/F detection unit 11 of the A/F sensor 10. Specifically, in the voltage supply unit 20, a constant power supply voltage Vcc is divided by resistors 21 and 22 and the divided voltage V0 is supplied to a non-inverting input terminal of an operational amplifier 23. The constant power supply voltage Vcc is divided by resistors 24 and 25 and the divided voltage Vp1 is supplied to a non-inverting input terminal of an operational amplifier 26. The voltages V0 and Vp1 are applied to the electrodes 15a and 15b of the A/F sensor 10 via the operational amplifiers 23 and 26, respectively. In the A/F detection unit 11, the limit current flows in the solid electrolyte layer 14 by the passage of oxygen ions according to the air-fuel ratio at that time and is detected as a limit current value Ip1 by a current detection resistor 41 of the current detecting unit 40. The limit current value Ip1 is outputted to a microcomputer (MC) 51 via an A/D converter 50 serving as the A/F output part. The value of resistance of the current detection resistor 41 is r.

On the other hand, the control unit 30 controls the amount of oxygen in the atmosphere chamber 18 at any air-fuel ratio. Specifically, the control unit 30 has a circuit for controlling the current flowing between the electrodes 15c and 15d. The control unit 30 is constructed as a voltage-current converting circuit using operational amplifiers 31 and 32. Both ends of the current detection resistor 41 are connected to two input terminals of the operational amplifier 31 via a voltage follower circuit constructed by operational amplifiers 33 and 34. The value of resistance of each of resistors 35 and 36 is Ri and the value of resistance of each of resistors 37 and 38 is R2. The current flowing in the solid electrolyte layer 16 in the oxygen supply/exhaust unit 12 is detected by a current detection resistor 61 in the current detection unit 60. The value of resistance of the current detection resistor 61 is r'.

In this case, when the values of resistance of the resistors 35 and 36 are R1 and the values of resistance of the resistors 37 and 38 are R2, current value Ip2 flowing in the solid electrolyte layer 16 of the oxygen supply/exhaust unit 12 is controlled by the following value.

$$Ip2 = (Ip1 \cdot r)/r'$$

When the value (r) of resistance of the current detection resistor 41 and the value (r') of resistance of the current detection resistor 61 are equal, the following relation holds.

Ip2=Ip1

The air-fuel ratio detecting apparatus of this embodiment operates as follows.

In the A/F sensor 10, a predetermined application voltage Vp1–V0 is applied across the pair of electrodes 15a and 15b in the A/F detection unit 11 and the A/F sensor 10 outputs the limit current value Ip according to the air-fuel ratio at that time. The limit current value Ip is detected as a voltage across the current detection resistor 41 in the current detection unit 40 and the detection value is outputted to the microcomputer 51 via the A/D converter 50.

The detected limit current value Ip is applied by the control unit 30. In this case, the current value Ip2 flowing in the solid electrolyte layer 16 on the oxygen supply/exhaust unit 12 is controlled so as to be equal to the limit current value Ip1 flowing in the solid electrolyte layer 14 of the A/F detection unit 11. Consequently, the amounts of oxygen passing through the two solid electrolyte layers 14 and 16 become equal. Even when the air-fuel ratio is shifted to either the lean side or the rich side, the oxygen partial pressure in the atmosphere chamber 18 is controlled to be constant.

That is, in the case where oxygen in the exhaust is taken into the atmosphere chamber 18 by the solid electrolyte layer 14 in the A/F detection unit 11 when the air-fuel ratio is on the lean side, oxygen is exhausted from the atmosphere chamber 18 to the outside by the solid electrolyte layer 16 in the oxygen supply/exhaust unit 12. In the case where oxygen in the atmosphere chamber 18 is consumed by the solid electrolyte layer 14 in the A/F detection unit 11 when the air-fuel ratio is on the rich side, oxygen is forcedly taken from the exhaust gas into the atmosphere chamber 18 by the solid electrolyte layer 16 in the oxygen supply/exhaust unit 12. Consequently, the oxygen partial pressure in the atmosphere chamber 18 can be always held to be constant.

In the control unit 30, when a feedback loop is formed by an application voltage Vp2 and the current value Ip2, a negative feedback system such that when the current value Ip2 increases, the application voltage Vp2 is reduced in order to control the Ip2 value to be constant is constructed. According to the construction, when internal resistance Ri of the solid electrolyte layer 16 changes, the current value Ip2 is changed accordingly. For example, when the temperature of the exhaust gas fluctuates at the time of excessive operation of the engine, the internal resistance Ri of the solid electrolyte layer 16 decreases and the Ip2 value increases, a potential (potential at A-point at an end of the current detection resistor 61, that is, the application voltage Vp2 decreases. The output of the operational amplifier 32 and also that of the operational amplifier 31 accordingly decrease. Thus, the increase in the Ip2 value is suppressed and the Ip2 value is held at a predetermined value. Thus, the operational amplifiers 31 and 32 in the control unit 30 monitor control current.

According to the embodiment described above in detail, the following effects can be obtained.

Figure 14A:
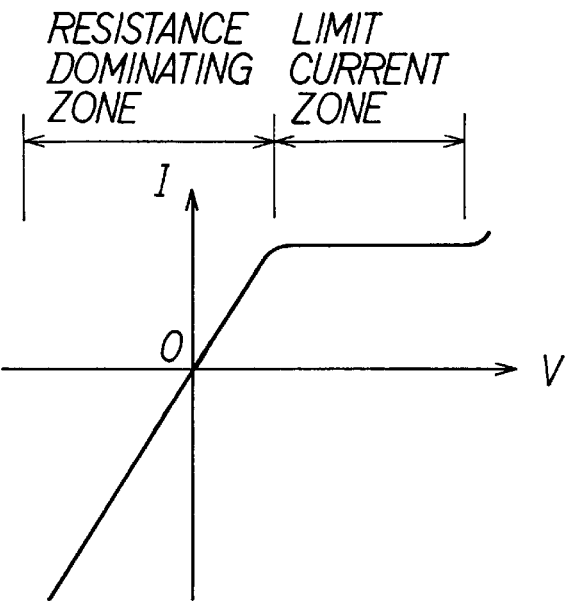
FIGS. 14A to 14C are diagrams for explaining output characteristics of the conventional air-fuel ratio sensor.
Figure 14B:
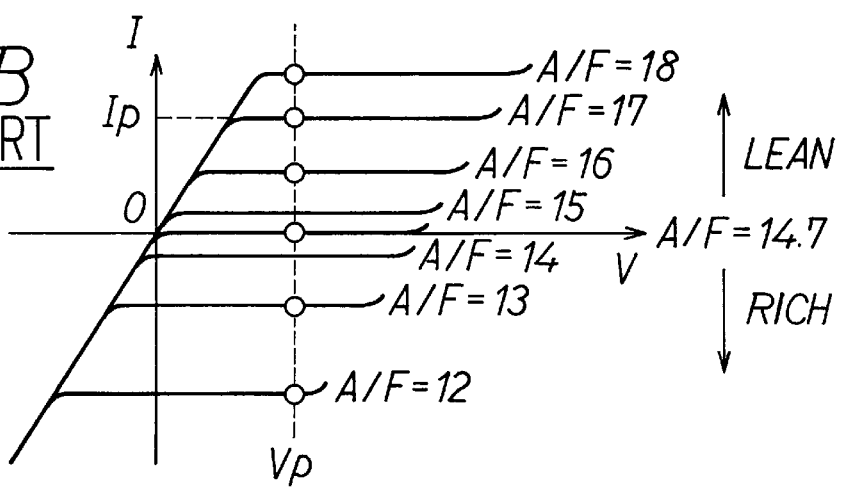
Figure 14C:
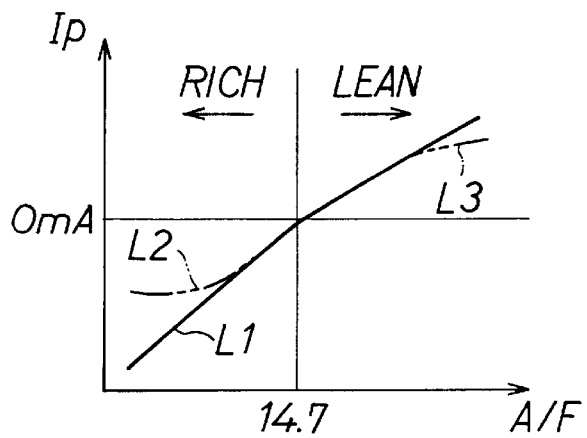

(A) In the embodiment, the limit current value Ip1 flowing in the solid electrolyte layer 14 is detected and the amount of supply or exhaust of oxygen by the oxygen supply/exhaust unit 12 is controlled on the basis of the limit current value Ip1. According to this operation, the fluctuation of the concentration of oxygen in the atmosphere chamber 18 is suppressed and the oxygen supply/exhaust unit 12 properly supplies or exhausts oxygen. That is, for example, deterioration in the air-fuel ratio detection accuracy due to the oxygen deficiency as shown by a characteristic line L2 in FIG. 14C or deterioration in the air-fuel ratio detection accuracy due to oxygen surplus as shown by a characteristic line L3 in FIG. 14C is solved. Consequently, the air-fuel ratio can be accurately detected in any air-fuel ratio zone. The atmosphere chamber 18 need not be enlarged more than needed and the temperature increasing characteristic of the element (solid electrolyte layer 14) is not deteriorated.

(B) Especially in the embodiment, the amount of supply or exhaust of oxygen by the oxygen supply/exhaust unit 12 is controlled by variably setting a control target value of the current flowing in the solid electrolyte layer 16 in the oxygen supply/exhaust unit 12. Specifically, the value Ip1 of the limit current flowing in the solid electrolyte layer 14 is used as a control target value of the current. According to this control, the amounts of oxygen flowing in the solid electrolyte layers 14 and 16 are always held equal, the concentration of oxygen in the atmosphere chamber 18 is stabilized and the detection accuracy of the air-fuel ratio can be improved as mentioned above.

(C) The current value Ip2 of the solid electrolyte layer 16 is detected and also monitored, and the value is always maintained to the target value. In this case, for example, even when the element temperature (the temperature of the solid electrolyte layer 16) rapidly changes at the time of excessive operation of the engine or in the event of fuel cut-off, the amount of supply or exhaust of oxygen by the oxygen supply/exhaust unit 12 can be stabilized.

(D) Further, according to the embodiment, the oxygen supply/exhaust unit 12 is constructed by a negative feedback system. Different from a conventional existing apparatus having a positive feedback system (for instance, an air-fuel ratio sensor of a 2-cell type), an inconvenience such that a current value or a voltage value oscillates can be solved.

(Second embodiment)

Figure 5:
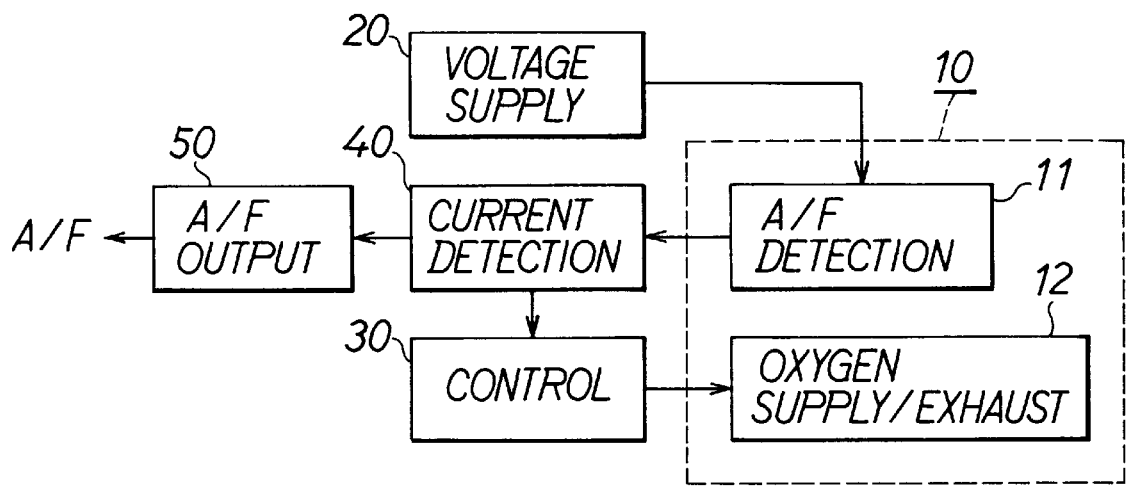
FIG. 5 is a block diagram showing an air-fuel ratio detecting apparatus according to a second embodiment of the present invention.

A second embodiment of the invention will be described with reference to FIGS. 5 and 6.

In this embodiment, the current detection unit 60 for detecting the current flowing in the oxygen supply/exhaust unit 12 in the A/F sensor 10 is omitted. In this case, the control unit 30 determines the controlled variable for the oxygen supply/exhaust unit 12 by the limit current value detected by the current detection unit 40. In this embodiment, the value of voltage applied to the oxygen supply/exhaust unit 12 corresponds to the controlled variable by the control unit 30.

Figure 6:
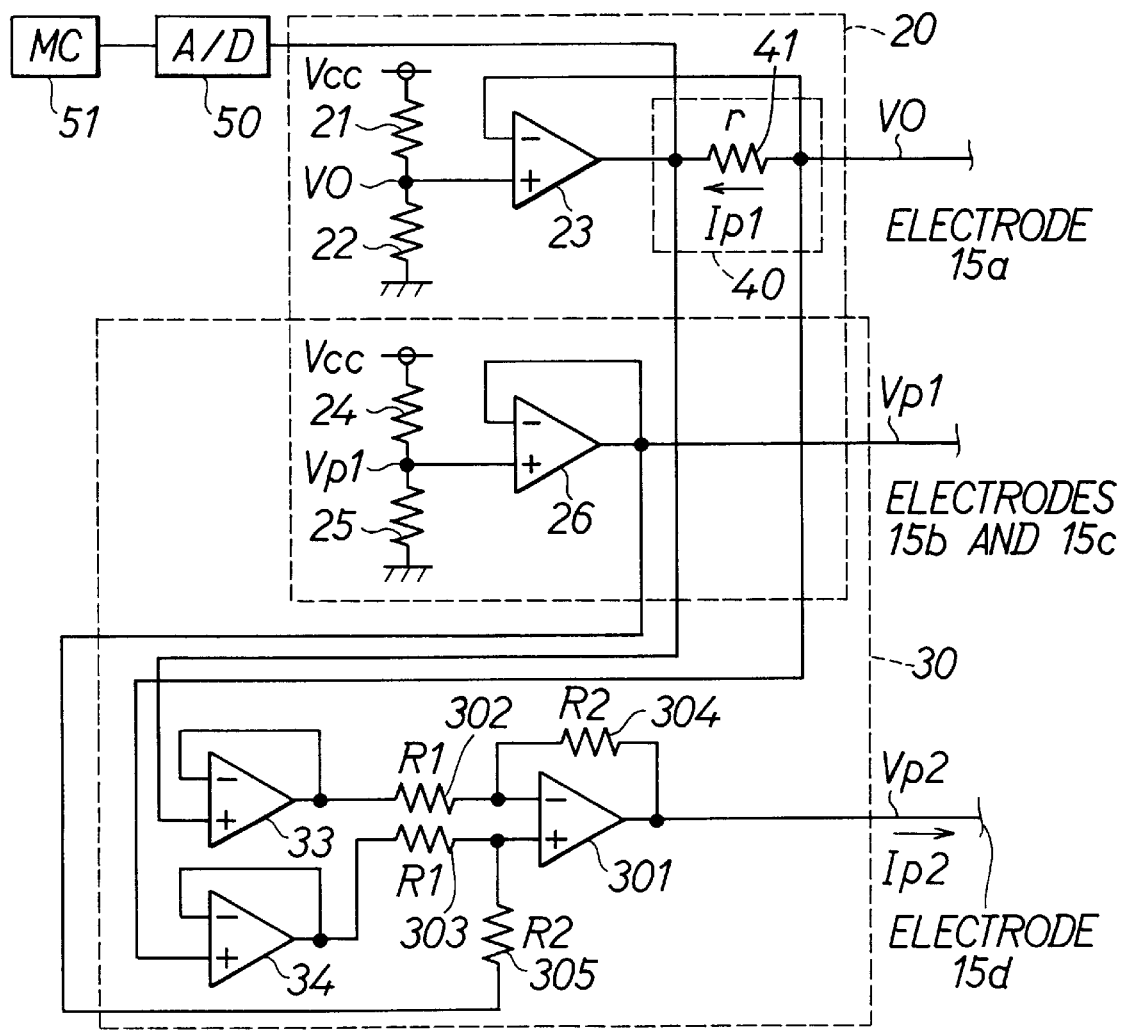
FIG. 6 is a circuit diagram showing the air-fuel ratio detecting apparatus according to the second embodiment.

FIG. 6 is a circuit diagram of the air-fuel ratio detecting apparatus in the embodiment. Only the control unit 30 in the diagram is different from the first embodiment. The control unit 30 multiplies the limit current value Ip (the difference between the voltages at both ends of the resistor 41) detected by the current detection resistor 41 by a constant in a differential amplifying circuit 301 by an operational amplifier. An application voltage Vp2 obtained by multiplication by a constant in the differential amplifying circuit 301 is used as a controlled variable and is applied to the oxygen supply/exhaust unit 12. The value of resistance of each of resistors 302 and 303 in the diagram is R1 and the value of resistance of each of resistors 304 and 305 is R2. In this case, the differential amplifying circuit 301 is offset by a reference voltage Vp1 applied to the A/F detection unit 11.

With this circuit construction, when the value of internal resistance of the solid electrolyte layer 16 is set to Ri, the application voltage Vp2 as a controlled variable to the oxygen supply/exhaust unit 12 is obtained as follows.

Vp2=Ip2·Ri+Vp1

The value Ip2 of the current flowing in the oxygen supply/exhaust unit 12 has the following relation with the value Ip1 of the limit current flowing in the A/F detection unit 11.

$$Ip2=(Ip1 \cdot r \cdot R2)/(Ri \cdot R1)$$

In such a case, when the amplification factor (R2/R1) of the differential amplifying circuit 301 is set so as to be equal to the ratio (Ri/r) of the internal resistance value Ri of the solid electrolyte layer 16 and the resistance value (r) of the current detection unit 41, the Ip1 value and the Ip2 value are equalized. When they are equal, the amounts of oxygen flowing in the solid electrolyte layers 14 and 16 are equal. Consequently, even when the air-fuel ratio changes, the oxygen partial pressure in the atmosphere chamber 18 can be held to be constant.

The application voltage Vp2 of the oxygen supply/exhaust unit 12 is obtained as follows.

$$Vp2=Ip1 \cdot r \cdot (R2/R1)+Vp1=Ip1 \cdot r \cdot (Ri/r)+Vp1$$

The internal resistance value Ri of the solid electrolyte layer 16 is a known value. It is sufficient that the value when the sensor is active is about 30 Ω.

In the second embodiment, the applied voltage vp2 across the pair of electrodes 15c and 15d formed on the solid electrolyte layer 16 is controlled, thereby controlling the amount of supply or exhaust of oxygen by the oxygen supply/exhaust unit 12. Consequently, an inconvenience such that the detection accuracy of the air-fuel ratio deteriorate due to oxygen deficiency or oxygen surplus in the atmosphere chamber 18 (reference gas side) can be solved.

According to the embodiment, the air-fuel ratio can be detected with high accuracy even when the air-fuel ratio changes as along as the relation of (R2/R1)=(Ri/r) can be maintained in the active state of the A/F sensor 10. When it is assumed that the element temperature (temperature of the solid electrolyte layer 16) rapidly changes and (R2/R1)≠(Ri/r), however, the Vp2 value cannot be held at a predetermined value. In an actual operation, it is therefore preferable to variably control the value of (R2/R1) so as to maintain the relation of (R2/R1)=(Ri/r) even when the internal resistance value Ri of the solid electrolyte layer 16 accompanying the change in element temperature changes.

Since the second embodiment has the construction in which the applied voltage Vp2 of the oxygen supply/exhaust unit 12 is open-controlled, different from the conventional existing apparatus having a positive feedback system (for example, an air-fuel ratio sensor of a 2-cell type), the oscillation phenomenon of the current or voltage value can be solved.

(Third Embodiment)

Figure 7:
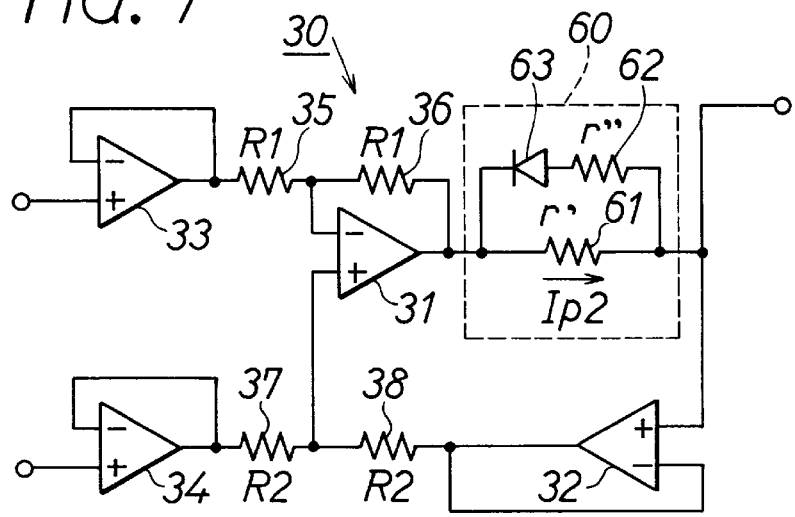
FIG. 7 is a circuit diagram showing a control unit of an air-fuel ratio detecting apparatus according to a third embodiment of the present invention.

In this embodiment, as shown in FIG. 7, a resistor 62 and a diode 63 are connected in parallel to the current detection resistor 61 in the current detection unit 60.

According to the construction, when the air-fuel ratio is on the rich side, oxygen ions pass through the second solid electrolyte layer 16 shown in FIG. 4 and move into the atmosphere chamber 18, thereby flowing a current to both of the resistors 61 and 62. When the air-fuel ratio is on the lean side, oxygen ions are moved in the opposite direction and consequently a current flows only into the resistor 61. If the following relation is satisfied among the values r' and r of resistance of the resistors 61 and 62 and the value (r) of resistance of the resistor 41 in FIG. 4, $$r' \cdot r/(r+r')<r<r'$$

when oxygen ions pass through the first solid electrolyte layer 14 in FIG. 4 and move into the atmosphere chamber 18 (when the air-fuel ratio is on the lean side), $$Ip2<Ip1$$

is obtained from the relational equation of the Ip1 and Ip2 values in the first embodiment. On the contrary, when oxygen ions move from the atmosphere chamber 18 to the first solid electrolyte layer 14 (when the air-fuel ratio is on the rich side), $$Ip2>Ip1$$

is obtained.

That is, when the air-fuel ratio is on the lean side, the amount of oxygen exhausted by the oxygen supply/exhaust unit 12 is regulated to a relatively small amount. When the air-fuel ratio is on the rich side, a relatively large amount of oxygen is allowed to be supplied. Consequently, even when oxygen tends to be excessive in the atmosphere chamber 18, oxygen deficiency is not caused. In this case, since the detection itself of the air-fuel ratio can be continued even in an oxygen excess state, the worst situation such that the air-fuel ratio cannot be detected due to the oxygen deficient state can be avoided. When r=r' is assumed, it can be also constructed so that Ip2=Ip1 when the air-fuel ratio is on the lean side.

In short, although the limit current value is deviated when the oxygen in the atmosphere chamber 18 is excessive, change in the current value (air-fuel ratio) can be sufficiently read and the air-fuel ratio control in the ECU can be continuously performed. On the contrary, when the oxygen in the atmosphere chamber 18 is deficient, since the limit current does not change even if the air-fuel ratio is shifted to the rich side, the change in the air-fuel ratio cannot be read. Consequently, the air-fuel ratio control cannot be performed and it is feared that an inconvenience of deterioration in drivability or fuel consumption is caused. From the above reasons, it is desirable that the oxygen in the atmosphere chamber 18 is in the excessive state more than the deficient state. If the atmosphere chamber 18 is in the oxygen excessive state, an influence on the air-fuel ratio control can be minimized.

(Fourth Embodiment)

Figure 8:
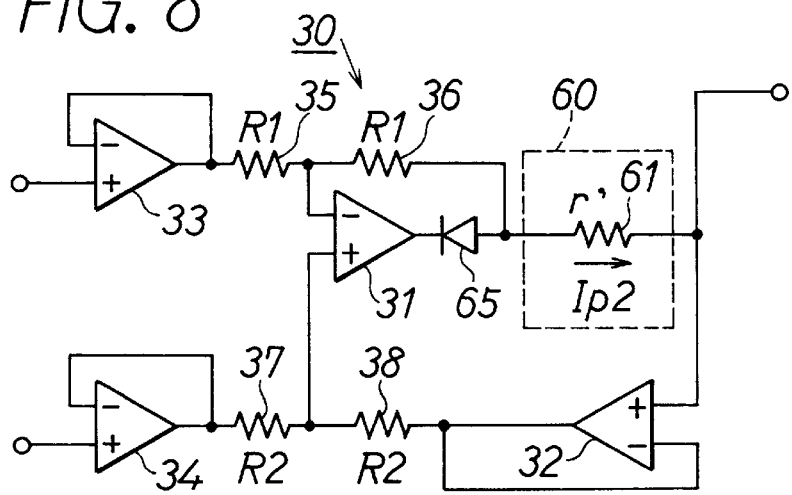
FIG. 8 is a circuit diagram showing a control unit of an air-fuel ratio detecting apparatus according to a fourth embodiment of the present invention.

In the fourth embodiment, as shown in FIG. 8, a diode 65 in the opposite direction is added to the output of the operational amplifier 31 and the direction of the current flowing in the second solid electrolyte layer 16 is specified.

According to this embodiment of FIG. 8, when oxygen is taken from the atmosphere chamber 18 to the outside of the first solid electrolyte layer 14, that is only when the air-fuel ratio is on the rich side, oxygen is supplied to the atmosphere chamber 18 by the oxygen supply/exhaust unit 12. That is, the oxygen deficient state of the atmosphere chamber 18 is limited to the time when the air-fuel ratio is on the rich side. By allowing the oxygen supplying operation to be performed only in such a case, an adverse effect on the air-fuel ratio control can be suppressed.

In case of FIG. 8, by equalizing the value r' of resistance of the current detection resistor 61 with the value r of resistance of the current detection resistor 41 in FIG. 4 (r'=r), the amounts of oxygen flowing in the two solid electrolyte layers 14 and 16 become equal and the concentration of oxygen in the atmosphere chamber 18 can be kept to be constant. If (r'<r), in a manner similar to FIG. 7, the concentration of oxygen in the atmosphere chamber 18 can be always maintained at an excess level.

(Fifth Embodiment)

Figure 9:
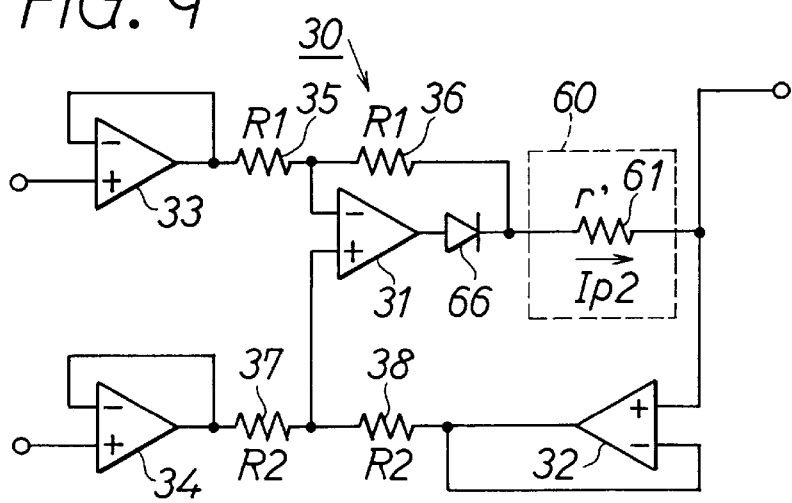
FIG. 9 is a circuit diagram showing a control unit of an air-fuel ratio detecting apparatus according to a fifth embodiment of the present invention.

In this embodiment, as shown in FIG. 9, a diode 66 is provided in a forward direction of the output of the operational amplifier 31. That is, the diode 66 is provided in the direction opposite to the diode 65 in FIG. 8.

According to FIG. 9, when oxygen is taken from the outside of the first solid electrolyte layer 14 into the atmosphere chamber 18, that is only when the air-fuel ratio is on the lean side, oxygen is exhausted from the atmosphere chamber 18 by the oxygen supply/exhaust unit 12. That is, the oxygen excess state of the atmosphere chamber 18 is limited to the time when the air-fuel ratio is on the lean side, and the oxygen exhausting operation is allowed to be performed only in such a case. For example, when the invention is applied to a sensor such as a lean sensor which does not require the detection accuracy on the rich side, by completely avoiding the excessive oxygen state in the atmosphere chamber 18, the air-fuel ratio (the concentration of oxygen) at the time of detection on the lean side can be detected with high accuracy.

(Sixth embodiment)

Figure 10:
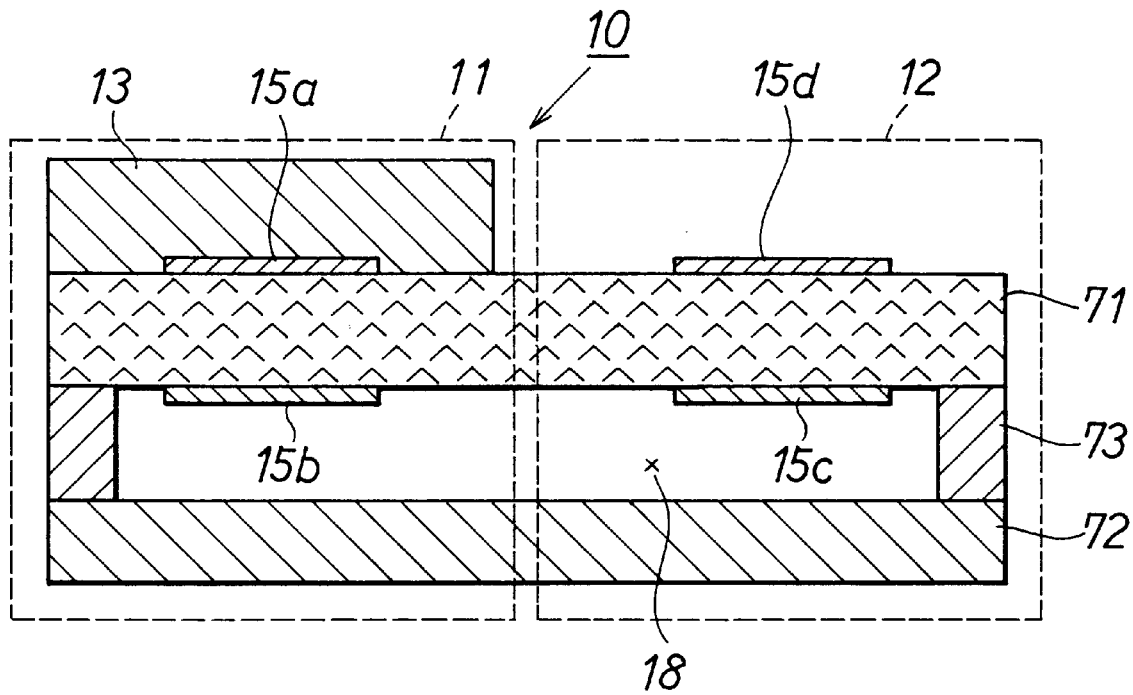
FIG. 10 is a cross sectional view showing an A/F sensor according to a sixth embodiment of the present invention.

In this embodiment, as shown in FIG. 10, the solid electrolyte layer 14 in the A/F detection unit 11 and the solid electrolyte layer 16 in the oxygen supply/exhaust unit 12 are used as a common solid electrolyte layer 71. In the A/F sensor 10, an insulating plate 72 having almost the same size as that of the solid electrolyte layer 71 is provided below the solid electrolyte layer 71 and the atmosphere chamber 18 partitioned by partition walls 73 is formed between the solid electrolyte layer 71 and the insulating plate 72.

(Seventh embodiment)

Figure 11:
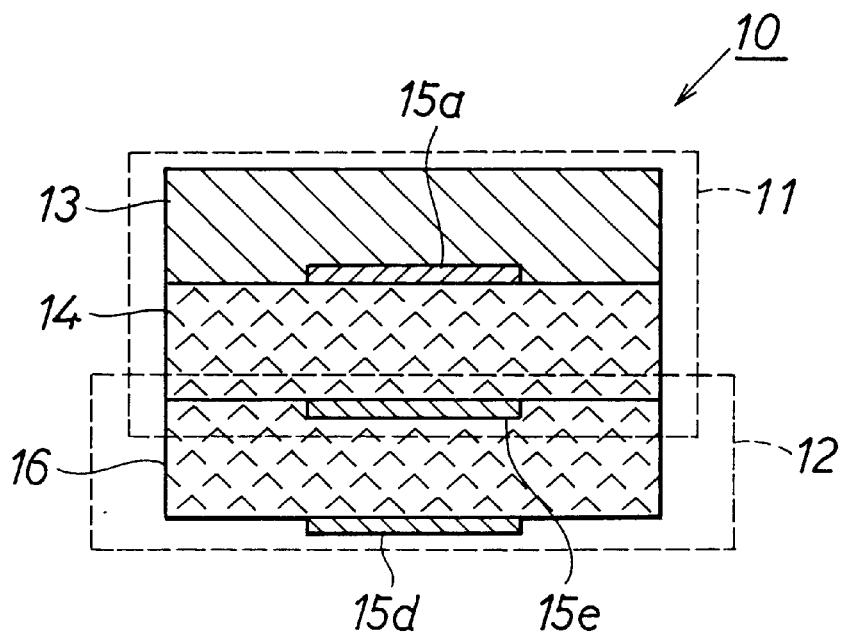
FIG. 11 is a cross sectional view showing an A/F sensor according to a seventh embodiment of the present invention.
Figure 12:
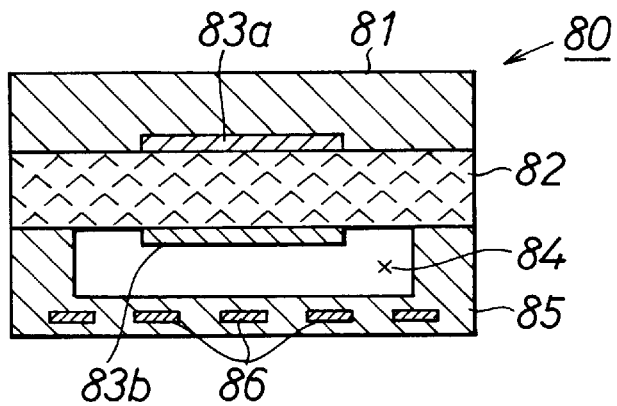
FIG. 12 is a cross sectional view showing a conventional air-fuel ratio sensor.
Figure 13A:
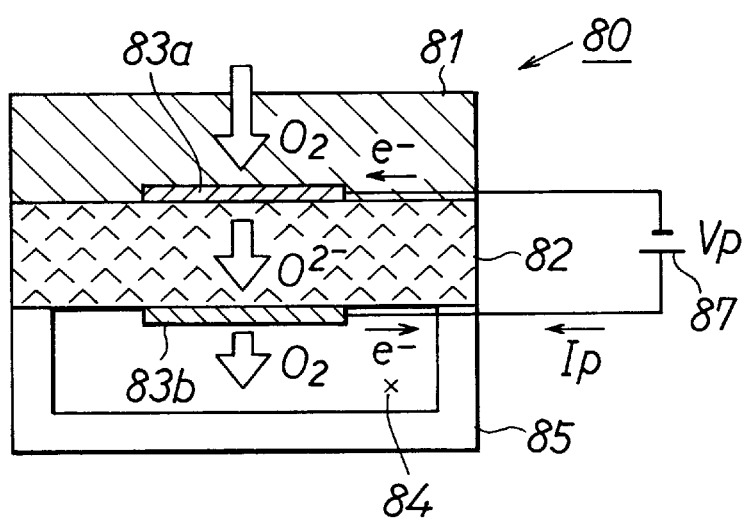
FIGS. 13A and 13B are diagrams for explaining the principle of the operation of the conventional air-fuel ratio sensor.
Figure 13B:
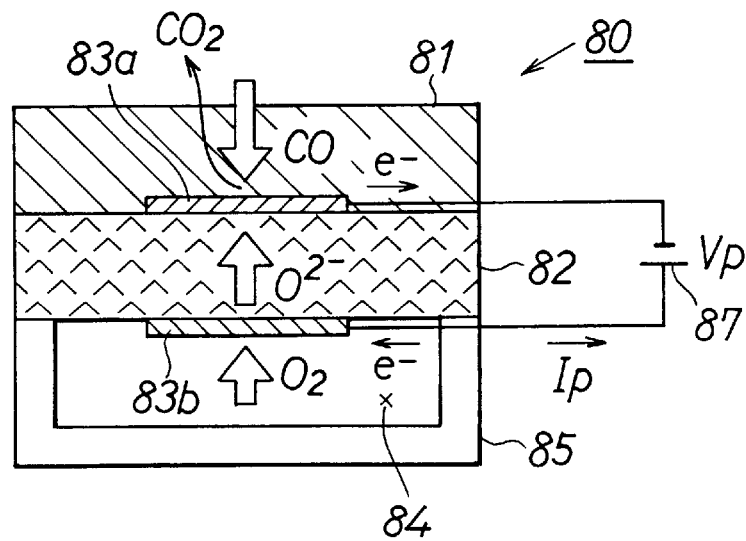

In the A/F sensor 10 of FIG. 11, the atmosphere chamber 18 between the A/F detection unit 11 and the oxygen supply/exhaust unit 12 is not provided. The electrodes 15b and 15c on the atmosphere side of the A/F detection unit 11 and the oxygen supply/exhaust unit 12 are commonly used as an electrode 15e (electrode on the reference gas side).

In either embodiments of FIG. 10 or 11, advantages similar to those of the A/F sensor of FIG. 2 can be obtained. That is, according to an air-fuel ratio detection apparatus using the A/F sensor 10 of FIG. 10 or 11, in a manner similar to the foregoing embodiments, the inconvenience such that the detection accuracy of the air-fuel ratio deteriorates due to oxygen deficiency or oxygen surplus on the reference gas side can be solved. An excellent effect such that the air-fuel ratio can be accurately detected in any air-fuel ratio zone can be obtained. Especially, according to FIG. 11, since the atmosphere chamber is unnecessary, the size of the sensor can be reduced.

Although the control unit 30 for controlling the amount of oxygen to the oxygen supply/exhaust unit 12 is embodied in an analog circuit in the foregoing embodiments, it can be also embodied in software by a microcomputer or the like. In this case, the microcomputer receives the limit current value Ip in the A/F detection unit 11 and controls the amount of supply or exhaust of oxygen by the oxygen supply/exhaust unit 12 in accordance with the Ip value.

Although the voltage applied to the A/F detection unit 11 (for example, V0 and Vp1 in FIG. 4) is set to be constant in the foregoing embodiments, the application voltage can be also variably controlled. For example, in case of controlling the application voltage so as to follow the limit current zone which changes by the change in air-fuel ratio or the change in the element temperature and in case of alternately changing the application voltage in order to detect the internal resistance of the solid electrolyte layer 14, a construction in which the application voltage is variably controlled can be also used. With such a construction as well, the object of the invention can be achieved in a manner similar to the foregoing embodiments.

What is claimed is:

1. An oxygen concentration detecting apparatus comprising:

an oxygen concentration detecting unit including a first solid electrolyte layer having a reference gas side face and a measured gas side face, a diffusion resistance layer in contact with the first solid electrolyte layer, and a pair of electrodes formed on both said faces of the first solid electrolyte layer, the first solid electrolyte layer being for generating a limit current value according to concentration of oxygen in a measured gas when a voltage is applied to said electrodes;

an oxygen supply/exhaust unit including a second solid electrolyte layer having a reference gas side face and a measured gas side face and a pair of electrodes formed on both said faces of the second solid electrolyte layer, the supply/exhaust unit selectively one of supplying oxygen to the electrode on the reference gas side thereof and exhausting oxygen to the electrode on the measured gas side thereof;

current detection means for detecting a value of a limit current flowing in the first solid electrolyte layer; and control means for controlling an amount of supply or exhaust of oxygen of the oxygen supply/exhaust unit in accordance with the detected limit current value, wherein:

the control means variably sets a control target value of a current flowing in the second solid electrolyte layer, thereby controlling the amount of supply or exhaust of oxygen of the oxygen supply/exhaust unit, the control means has a current detection means for detecting the value of a current flowing in the second solid electrolyte layer; and the control means has control current monitoring means for monitoring the current value detected by the current detection means of the control means and maintaining the monitored current value to a target value.

2. The apparatus according to claim 1, wherein:

the control means controls the amount of supply or exhaust of oxygen of the oxygen supply/exhaust unit so that the amount of oxygen moving in the first solid electrolyte layer and the amount of oxygen moving in the second solid electrolyte layer are equal.

3. The apparatus according to claim 1, wherein:

when oxygen moves from the measured gas side to the reference gas side in the first solid electrolyte layer, the control means controls the amount of supply or exhaust of oxygen of the oxygen supply/exhaust unit by allowing oxygen of an amount smaller than a moved amount of said oxygen in the first solid electrolyte layer to be moved from the reference gas side to the measured gas side in the second solid electrolyte layer, and when oxygen moves from the reference gas side to the measured gas side in the first solid electrolyte layer, the control means controls the amount of supply or exhaust of oxygen of the oxygen supply/exhaust unit by allowing oxygen of an amount larger than a moved amount of said oxygen in the first solid electrolyte layer to be moved from the measured gas side in the second solid electrolyte layer to the reference gas side.

4. The apparatus according to claim 1, wherein:

the control means variably controls a control target value of a voltage applied across the pair of electrodes formed on the second solid electrolyte layer, thereby controlling the amount of supply or exhaust of oxygen by the oxygen supply/exhaust unit.

5. The apparatus according to claim 1, wherein:

the control means is operated only when oxygen moves from the reference gas side to the measured gas side in the first solid electrolyte layer.

6. The apparatus according to claim 1, wherein:
the control means is operated only when oxygen moves from the measured gas side to the reference gas side in the first solid electrolyte layer.

7. The apparatus according to claim 1, wherein:
the first solid electrolyte layer and the second solid electrolyte layer are adjacent to each other and thereby form a single solid electrolyte layer.

8. The apparatus according to claim 1, wherein:
the first solid electrolyte layer and the second solid electrolyte layer are held in contact with each other with a single electrode element therebetween, said electrode element defining the reference gas side electrode of each said pair of electrodes.

9. An oxygen concentration detecting apparatus as in claim 1, wherein said diffusion resistance layer overlies the measured gas side face electrode of said pair of electrodes of the first solid electrolyte layer.

10. An oxygen concentration detecting method comprising the steps of:
applying a first voltage to an oxygen concentration detecting unit including a first solid electrolyte layer having a reference gas side face facing a reference gas chamber and a measured gas side face and a pair of electrodes formed on both said faces of the first solid electrolyte layer so that a limit current flows in the first solid electrolyte layer according to a difference in concentration of oxygen in a gas to be measured and in a reference gas in the reference gas chamber;
detecting a value of the limit current flowing in the first solid electrolyte layer;
applying a second voltage to an oxygen supply/exhaust unit including a second solid electrolyte layer having a reference gas side face and a measured gas side face and a pair of electrodes formed on both said faces of the second solid electrolyte layer so that the supply/exhaust unit selectively supplies or exhausts oxygen to and from the reference gas chamber; and
controlling the second voltage in accordance with the detected limit current value, wherein
the controlling step controls the second voltage to maintain substantially equally the amount of oxygen moving in the first solid electrolyte layer and the amount of oxygen moving in the second solid electrolyte depending on whether oxygen moves from or to the reference gas chamber through the first solid electrolyte layer.

11. An oxygen concentration detecting method comprising the steps of:
applying a first voltage to an oxygen concentration detecting unit including a first solid electrolyte layer having a reference gas side face facing a reference gas chamber and a measured gas side face and a pair of electrodes formed on both said faces of the first solid electrolyte layer so that a limit current flows in the first solid electrolyte layer according to a difference in concentration of oxygen in a gas to be measured and in a reference gas in the reference gas chamber;
detecting a value of the limit current flowing in the first solid electrolyte layer;
applying a second voltage to an oxygen supply/exhaust unit including a second solid electrolyte layer having a reference gas side face and a measured gas side face and a pair of electrodes formed on both said faces of the second solid electrolyte layer so that the supply/exhaust unit selectively supplies or exhausts oxygen to and from the reference gas chamber;
controlling the second voltage in accordance with the detected limit current value; and
detecting a value of a current flowing in the second solid electrolyte layer,
wherein the controlling step controls the second voltage to maintain substantially equally the two detected values of the currents flowing in the first solid electrolyte layer and the second solid electrolyte layer.

12. The method according to claim 11, wherein:
the controlling step controls the second voltage to maintain equally the amount of oxygen moving in the first solid electrolyte layer and the amount of oxygen moving in the second solid electrolyte.

13. An oxygen concentration detecting apparatus comprising:
a first solid electrolyte layer having a reference gas side face and a measured gas side face, a first electrode formed on said reference gas side of said first solid electrolyte layer, and a second electrode formed on said measured gas side face of the first solid electrolyte layer, said first and second electrodes and said first solid electrolyte layer disposed therebetween defining an oxygen concentration detecting unit whereby when a voltage is applied to said first and second electrodes, said first solid electrolyte layer generates a limit current value according to a concentration of oxygen in a measured gas disposed on said measured gas side of said first solid electrolyte layer;
an insulating layer;
a second solid electrolyte layer having a reference gas side face and a measured gas side face, a first electrode formed on said reference gas side face of the second solid electrolyte layer and a second electrode formed on the measured gas side face of the second solid electrolyte layer, said first and second electrodes and said second solid electrolyte layer disposed therebetween defining a supply/exhaust unit for selectively supplying/exhausting oxygen to one of the reference gas side thereof and the measured gas side thereof, said second solid electrolyte layer being disposed in opposed facing relation to said first solid electrolyte layer with said insulation layer disposed therebetween;
a reference gas chamber being defined in said insulating layer, said first electrode of each said solid electrolyte layer being disposed in communication with said reference gas chamber; and
a controller for controlling an amount and destination of oxygen supply of the oxygen supply/exhaust unit in accordance with the value of the limit current flowing in the first solid electrolyte layer, wherein:
the controller has a current detector for detecting the value of a current flowing in the second solid electrolyte layer; and
the controller has a control current monitor for monitoring the current value detected by the current detector of the controller and maintaining the monitored current value to a target value.

14. The apparatus according to claim 13, wherein:
the control means controls the amount of supply or exhaust of oxygen of the oxygen supply/exhaust unit so that the amount of oxygen moving in the first solid electrolyte layer and the amount of oxygen moving in the second solid electrolyte layer are equal.

15. The apparatus according to claim 14, wherein:

when oxygen moves from the measured gas side to the reference gas side in the first solid electrolyte layer, the control means controls the amount of supply or exhaust of oxygen of the oxygen supply/exhaust unit by allowing oxygen of an amount smaller than a moved amount of said oxygen in the first solid electrolyte layer to be moved from the reference gas side to the measured gas side in the second solid electrolyte layer, and when oxygen moves from the reference gas side to the measured gas side in the first solid electrolyte layer, the control means controls the amount of supply or exhaust of oxygen of the oxygen supply/exhaust unit by allowing oxygen of an amount larger than a moved amount of said oxygen in the first solid electrolyte layer to be moved from the measured gas side in the second solid electrolyte layer to the reference gas side.

16. The apparatus according to claim 13, wherein:

the control means variably sets a control target value of a current flowing in the second solid electrolyte layer, thereby controlling the amount of supply or exhaust of oxygen of the oxygen supply/exhaust unit.

17. The apparatus according to claim 13, wherein:

the control means variably controls a control target value of a voltage applied across the pair of electrodes formed on the second solid electrolyte layer, thereby controlling the amount of supply or exhaust of oxygen by the oxygen supply/exhaust unit.

* * * * *